(12) United States Patent
Majumdar

(10) Patent No.: US 6,399,743 B1
(45) Date of Patent: Jun. 4, 2002

(54) ISOLATION AND CHARACTERIZATION OF A RAT EPIDERMAL GROWTH FACTOR RELATED PROTEIN

(75) Inventor: Adhip P. N. Majumdar, W. Bloomfield, MI (US)

(73) Assignee: Dept. of Veterans Affairs, Washington, DC (US)

( * ) Notice: Subject to any disclaimer, the term of this patent is extended or adjusted under 35 U.S.C. 154(b) by 0 days.

(21) Appl. No.: 09/570,454

(22) Filed: May 12, 2000

Related U.S. Application Data

(60) Provisional application No. 60/134,200, filed on May 14, 1999.

(51) Int. Cl.$^7$ ............................................... C07K 14/00
(52) U.S. Cl. ....................................... 530/324; 530/350
(58) Field of Search ................................ 530/350, 324; 435/6

(56) References Cited

PUBLICATIONS

Bargmann et al. The neu oncogne encodes an epidermal growth factor receptor–related protein. 1986. Nature, 319:226–30.*

\* cited by examiner

*Primary Examiner*—Yvonne Eyler
*Assistant Examiner*—Dong Jiang
(74) *Attorney, Agent, or Firm*—Blank Rome Comisky & McCauley LLP

(57) ABSTRACT

A cDNA fragment clone of 1583 base pairs with 90–95% sequence homology to the mouse EGFR and a truncated rat EGFR is described. The isolated cDNA is termed ERRP (EFG-Receptor Related Protein). In Northern-blot analysis with poly A+ RNA from different rat tissues, ERRP cDNA hybridized strongly to a mRNA transcript of about 1.8 kb. Maximal expression was noted in the small intestine, followed by colon, liver, gastric mucosa and other tissues. Transfection of ERRP cDNA in HCT-116 cells, a colon cancer cell line, markedly inhibits proliferation in monolayer and in soft agar and attenuates EGF-R tyrosine kinase activity. Transfection of ERRP in HCT-116 also delays tumor growth in SCID mice injected with these cells compared to the vector-transfector control cells. On the other hand, proliferation of the vector-transfected control, but not ERRP transfected HCT cells could be stimulated by TGF-α ($10^{-10}$M and $10^{-9}$M). The ERRP cDNA represents a new member of the EGFR gene family, and its protein product plays a key role in modulating the function of EGFR.

4 Claims, 9 Drawing Sheets

```
  1  GGGTGTTTTA TTTCCTCCTC TTCTTCCCGC ACTGTGCGCT CCTCCTGGGC TAGGGCGTCT

61  GGATCGAGTC CCGGAGGCTA CCGCCTCCCA GACAGACGAC GGGTCACCTG GACGCGAGCC

121  TGTGTCCGGG TCTCGTCGTT GCCGGCGCAG TCACTGGGCA CAACCGTGGG ACTCCGTCTG

181  TCTCGGATTA ATCCCGGAGA GCCAGAGCCA ACCTCTCCCG GTCAGAGATG CGACCCTCAG
  1                                                       Met ArgProSerG

241  GGACCGCGAG AACCACACTG CTGGTGCTGC TGACCGCGCT CTGCGCGGCA GGTGGGGCGT
  5  lyThrAlaAr gThrThrLeu LeuValLeuL euThrAlaLe uCysAlaAla GlyGlyAlaL

301  TGGAGGAAAA GAAAGTCTGC CAAGGCACAA GTAACAGGCT CACCCAACTG GGCACTTTTG
 25  euGluGluLy sLysValCys GlnGlyThrS erAsnArgLe uThrGlnLeu GlyThrPheG

361  AAGACCACTT TCTGAGCCTG CAGAGGATGT ACAACAACTG TGAAGTGGTC CTTGGGAACT
 45  luAspHisPh eLeuSerLeu GlnArgMetT yrAsnAsnCy sGluValVal LeuGlyAsnL

421  TGGAAATTAC CTATGTGCAA AGGAATTACG ACCTTTCCTT CTTAAAAACC ATCCAGGAGG
 65  euGluIleTh rTyrValGln ArgAsnTyrA spLeuSerPh eLeuLysThr IleGlnGluV

481  TGGCCGGCTA TTTCCTCATT GCCCTCAACA CCGTGGAGAG AATCCCTTCG GAGGACCTGC
 85  alAlaGlyTy rPheLeuIle AlaLeuAsnT hrValGluAr gIleProSer GluAspLeuG

541  AGATCATCAG GGGAAATGCT CTTTATGAAA ACACCTATGC CTTAGCCATC CTGTCCAACT
105  lnIleIleAr gGlyAsnAla LeuTyrGluA snThrTyrAl aLeuAlaIle LeuSerAsnT

601  ATGGGACAAA CAGAACTGGG CTTAGGGAAC TGCCCATGCG GAACTTACAG GAAATCCTGA
125  yrGlyThrAs nArgThrGly LeuArgGluL euProMetAr gAsnLeuGln GluIleLeuI

661  TTGGTGCTGT GCGATTCAGC AACAACCCCA TCCTCTGCAA TATGGATACT ATCCAGTGGA
145  leGlyAlaVa lArgPheSer AsnAsnProI leLeuCysAs nMetAspThr IleGlnTrpA

721  GGGACATCGT CCAAAACGTC TTTATGAGCA ACATGTCAAT GGACTTACAG AGCCATCCGA
165  rgAspIleVa lGlnAsnVal PheMetSerA snMetSerMe tAspLeuGln SerHisProS

781  GCAGTTGCCC CAAATGTGAT CCAAGCTGTC CCAATGGAAG CTGCTGGGGA GGAGGAGAGG
185  erSerCysPr oLysCysAsp ProSerCysP roAsnGlySe rCysTrpGly GlyGlyGluG

841  AGAACTGCCA GAAATTGACC AAAATCATCT GTGCCCAGCA ATGTTCCCAT CGCTGTCGTG
205  luAsnCysGl nLysLeuThr LysIleIleC ysAlaGlnGl nCysSerHis ArgCysArgG

901  GCAGGTCCCC CAGTGACTGC TGCCACAACC AATGTGCTGC GGGGTGTACA GGGCCCCAAA
225  lyArgSerPr oSerAspCys CysHisAsnG lnCysAlaAl aGlyCysThr GlyProGlnL
```

FIG. 1(a)

```
 961  AGAGTGACTG TCTGGTCTGC CAAAAGTTCC AAGATGAGGC CACATGCAAA GACACCTGCC
 245  ySSerAspCy sLeuValCys GlnLysPheG lnAspGluAl aThrCysLys AspThrCysP

1021  CACCACTCAT GCTGTACAAC CCCACCACCT ATCAGATGGA TGTCAACCCT GAAGGGAAGT
 265  roProLeuMe tLeuTyrAsn ProThrThrT yrGlnMetAs pValAsnPro GluGlyLysT

1081  ACAGCTTTGG TGCCACCTGT GTGAAGAACT GCCCCCGAAA CTACGTGGTG ACAGATCATG
 285  yrSerPheGl yAlaThrCys ValLysAsnC ysProArgAs nTyrValVal ThrAspHisG

1141  GCTCATGTGT CCGAGCCTGT GGGCCTGACT ACTACGAAGT GGAAGAAGAT GGCATCCGCA
 305  lySerCysVa lArgAlaCys GlyProAspT yrTyrGluVa lGluGluAsp GlyIleArgL

1201  AGTGTAAAAA ATGTGATGGG CCCTGTCGCA AAGTTTGTAA TGGCATAGGC ATTGGTGAAT
 325  ysCysLysLy sCysAspGly ProCysArgL ysValCysAs nGlyIleGly IleGlyGluP

1261  TTAAAGACAC ACTCTCCATA AATCGTACAA ACATCAAACA CTTCAAATAC TGCACTGCCA
 345  heLysAspTh rLeuSerIle AsnAlaThrA snIleLysHi sPheLysTyr CysThrAlaI

1321  TCAGCGGGGA CCTTCACATC CTGCCAGTGG CCTTTAAGGG GGATTCTTTC ACGCGCACTC
 365  leSerGlyAs pLeuHisIle LeuProValA laPheLysGl yAspSerPhe ThrArgThrP

1381  CTCCTCTAGA CCCACGGGAA CTAGAAATTC TCAAGACTGT GAAGGAAATA ACAGGGTCTT
 385  roProLeuAs pProArgGlu LeuGluIleL euLysThrVa lLysGluIle ThrGlySerL

1441  TGCTGATTCA GGCTTGGCCT GAAAACTGGA CTGACCTCCA TGCTTTTGAG AACCTAGAAA
 405  euLeuIleGl nAlaTrpPro GluAsnTrpT hrAspLeuHi sAlaPheGlu AsnLeuGluI

1501  TAATTCGTGG CAGAACAAAG CAACATGGTC AGTTTTCTCT GGCGGTTGTC GGCCTGAACA
 425  leIleArgGl yArgThrLys GlnHisGlyG lnPheSerLe uAlaValVal GlyLeuAsnI

1561  TAACATCGCT GCCGTGGCAG GTTCCATCGC TGTCGTGGCA GGCTGTGACA AGGCCCTTGC
 445  leThrSerLe uProTrpGln ValProSerL euSerTrpGl nAlaValThr ArgProLeuH

1621  ACCCTCTGGC CCAAAATAGA GTCAGCTGGG ACACTGGGCC CTGACCTTGT AAGCTTCCTG
 465  isProLeuAl aGlnAsnArg ValSerTrpA spThrGlyPr o---                     478

1681  TAATGTTAGC CTGCCCATGG CACCCCAACA GCAAGATCCT GAAGCTCAAG TTTGATCCTA

1741  ACAAAACCAC CGCTGCTGCG GTTTCTGGGA GAAGCAAGCA TTTATTCACC TGCAAGATCA

1801  CATCCCTAAC CTTGACTTTG CTTAAGAGTG CTGAATGAAG ATCCTGTCCC TAAATCATAA

1861  CTCAATTCTT TTGCTCAAGG AAAATGCACT TGTCTTCTTC CAAAAAAAAA AAATCAATAT

1921  GCAAAATGGA ATTTGAAATA AAAGCTTTTC TAAAAATG                              1958
```

FIG.1(b)

```
   1 GGGTGTTTTA TTTCCTCCTC TTCTTCCCGC ACTGTGCGCT CCTCCTGGGC TAGGGCGTCT
  61 GGATCGAGTC CCGGAGGCTA CCGCCTCCCA GACAGACGAC GGGTCACCTG GACGCGAGCC
 121 TGTGTCCGGG TCTCGTCGTT GCCGGCGCAG TCACTGGGCA CAACCGTGGG ACTCCGTCTG
 181 TCTCGGATTA ATCCCGGAGA GCCAGAGCCA ACCTCTCCCG GTCAGAGATG CGACCCTCAG
 241 GGACCGCGAG AACCACACTG CTGGTGCTGC TGACCGCGCT CTGCGCGGCA GGTGGGGCGT
 301 TGGAGGAAAA GAAAGTCTGC CAAGGCACAA GTAACAGGCT CACCCAACTG GGCACTTTTG
 361 AAGACCACTT TCTGAGCCTG CAGAGGATGT ACAACAACTG TGAAGTGGTC CTTGGGAACT
 421 TGGAAATTAC CTATGTGCAA AGGAATTACG ACCTTTCCTT CTTAAAAACC ATCCAGGAGG
 481 TGGCCGGCTA TTTCCTCATT GCCCTCAACA CCGTGGAGAG AATCCCTTCG GAGGACCTGC
 541 AGATCATCAG GGGAAATGCT CTTTATGAAA ACACCTATGC CTTAGCCATC CTGTCCAACT
 601 ATGGGACAAA CAGAACTGGG CTTAGGGAAC TGCCCATGCG GAACTTACAG GAAATCCTGA
 661 TTGGTGCTGT GCGATTCAGC AACAACCCCA TCCTCTGCAA TATGGATACT ATCCAGTGGA
 721 GGGACATCGT CCAAAACGTC TTTATGAGCA ACATGTCAAT GGACTTACAG AGCCATCCGA
 781 GCAGTTGCCC CAAATGTGAT CCAAGCTGTC CAATGGAAG CTGCTGGGGA GGAGGAGAGG
 841 AGAACTGCCA GAAATTGACC AAAATCATCT GTGCCCAGCA ATGTTCCCAT CGCTGTCGTG
 901 GCAGGTCCCC CAGTGACTGC TGCCACAACC AATGTGCTGC GGGGTGTACA GGGCCCCAAA
 961 AGAGTGACTG TCTGGTCTGC CAAAAGTTCC AAGATGAGGC CACATGCAAA GACACCTGCC
1021 CACCACTCAT GCTGTACAAC CCCACCACCT ATCAGATGGA TGTCAACCCT GAAGGGAAGT
1081 ACAGCTTTGG TGCCACCTGT GTGAAGAACT GCCCCCGAAA CTACGTGGTG ACAGATCATG
1141 GCTCATGTGT CCGAGCCTGT GGGCCTGACT ACTACGAAGT GGAAGAAGAT GGCATCCGCA
1201 AGTGTAAAAA ATGTGATGGG CCCTGTCGCA AGTTTGTAA TGGCATAGGC ATTGGTGAAT
1261 TTAAAGACAC ACTCTCCATA AATGCTACAA ACATCAAACA CTTCAAATAC TGCACTGCCA
1321 TCAGCGGGGA CCTTCACATC CTGCCAGTGG CCTTTAAGGG GGATTCTTTC ACGCGCACTC
1381 CTCCTCTAGA CCCACGGGAA CTAGAAATTC TCAAGACTGT GAAGGAAATA ACAGGGTCTT
1441 TGCTGATTCA GGCTTGGCCT GAAAACTGGA CTGACCTCCA TGCTTTTGAG AACCTAGAAA
1501 TAATTCGTGG CAGAACAAAG CAACATGGTC AGTTTTCTCT GGCGGTTGTC GGCCTGAACA
1561 TAACATCGCT GCCGTGGCAG GTTCCATCGC TGTCGTGGCA GGCTGTGACA AGGCCCTTGC
1621 ACCCTCTGGC CCAAAATAGA GTCAGCTGGG ACACTGGGCC CTGACCTTGT AAGCTTCCTG
1681 TAATGTTAGC CTGCCCATGG CACCCCAACA GCAAGATCCT GAAGCTCAAG TTTGATCCTA
1741 ACAAAACCAC CGCTGCTGCG GTTTCTGGGA GAAGCAAGCA TTTATTCACC TGCAAGATCA
1801 CATCCCTAAC CTTGACTTTG CTTAAGAGTG CTGAATGAAG ATCCTGTCCC TAAATCATAA
1861 CTCAATTCTT TTGCTCAAGG AAAATGCACT TGTCTTCTTC CAAAAAAAAA AAATCAATAT
1921 GCAAAATGGA ATTTGAAATA AAGCTTTTC TAAAAATG Poly-A
```

FIG. 2

```
MRPSGTARTTLLVLLTALCAAGGALEEKKVCQGTSNRLTQLGTFEDHFLSLQRMYNNCEVVLGNLEITYVQRNYDLSFL
KTIQEVAGYFLIALNTVERIPSEDLQIIRGNALYENTYALAILSNYGTNRTGLRELPMRNLQEILIGAVRFSNNPILCN
MDTIQWRDIVQNVFMSNMSMDLQSHPSSCPKCDPSCPNGSCWGGGEENCQKLTKIICAQQCSHRCRGRSPSDCCHNQCA
AGCTGPQKSDCLVCQKFQDEATCKDTCPPLMLYNPTTYQMDVNPEGKYSFGATCVKNCPRNYVVTDHGSCVRACGPDYY
EVEEDGIRKCKKCDGPCRKVCNGIGIGEFKDTLSINATNIKHFKYCTAISGDLHILPVAFKGDSFTRTPPLDPRELEIL
KTVKEITGSLLIQAWPENWTDLHAFENLEIIRGRTKQHGQFSLAVVGLNITSLPWQVPSLSWQAVTRPLHPLAQNRVSW
DTGP*
```

FIG. 3

FIG. 4 SCHEMATIC MAP OF RAT ERRP cDNA

FIG. 9 CLONOGENIC ASSAY
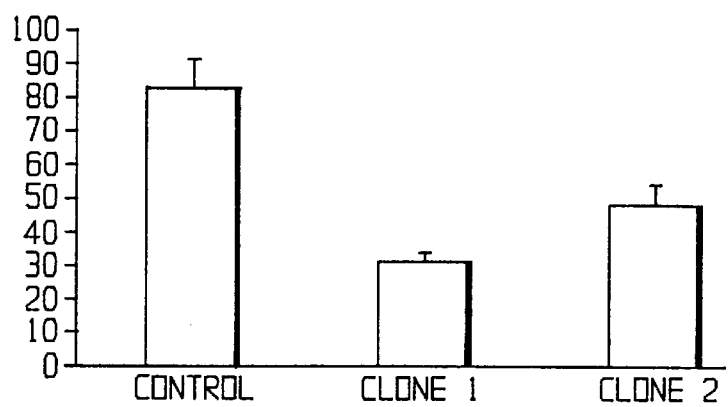
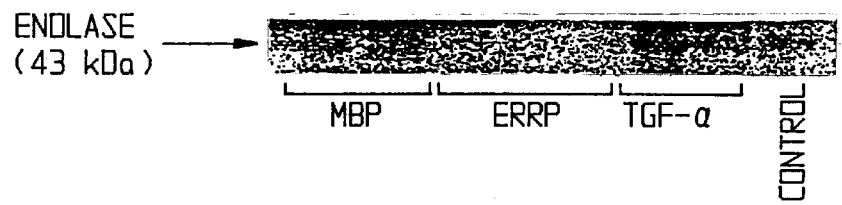
FIG. 11
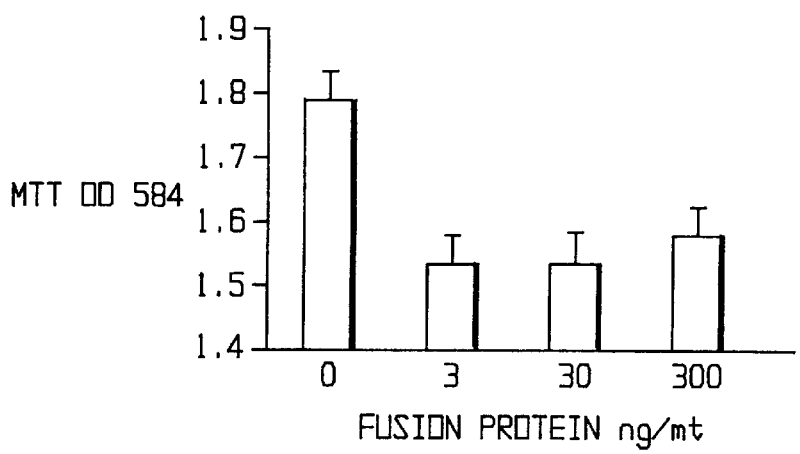
FIG. 12

FIG. 13 TUMOR GROWTH IN SCID MICE XENOGRAFTS
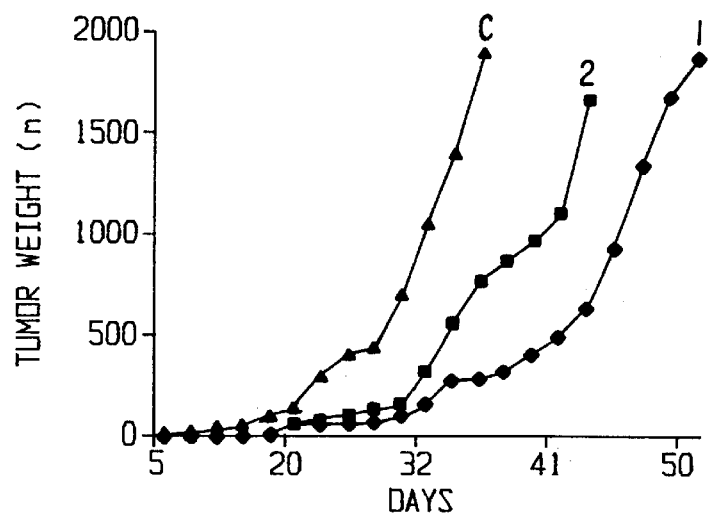
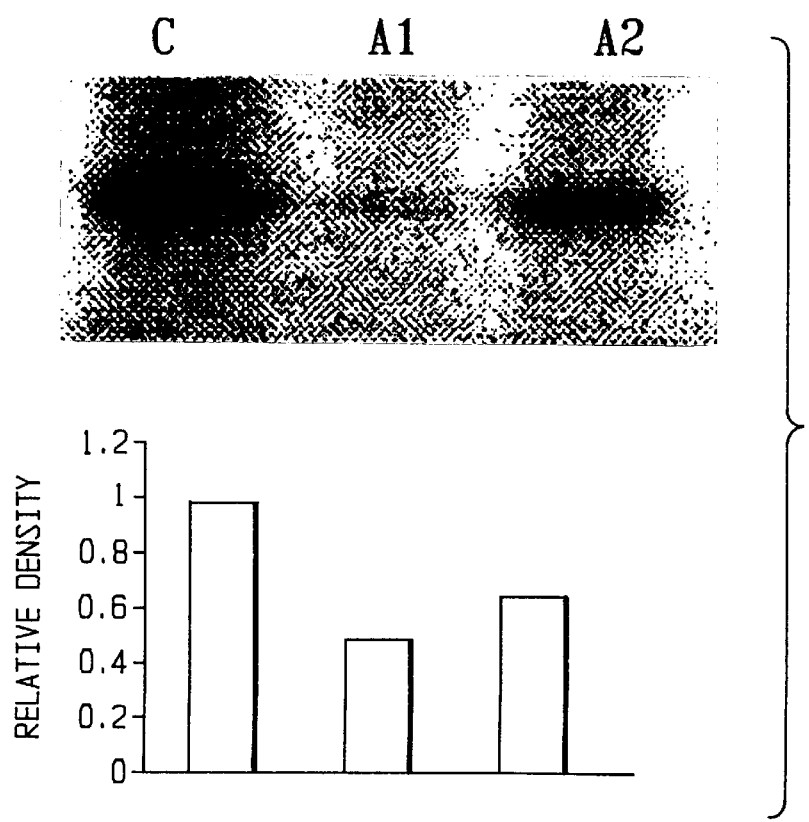
FIG. 14

SEQUENCE LISTING

<160> NUMBER OF SEQ ID NOS: 8

<210> SEQ ID NO 1
<211> LENGTH: 1958
<212> TYPE: DNA
<213> ORGANISM: Rattus norvegicus

<400> SEQUENCE: 1

```
gggtgtttta tttcctcctc ttcttcccgc actgtgcgct cctcctgggc tagggcgtct      60
ggatcgagtc ccggaggcta ccgcctccca gacagacgac gggtcacctg gacgcgagcc     120
tgtgtccggg tctcgtcgtt gccggcgcag tcactgggca caaccgtggg actccgtctg     180
tctcggatta atcccggaga gccagagcca acctctcccg gtcagagatg cgaccctcag     240
ggaccgcgag aaccacactg ctggtgctgc tgaccgcgct ctgcgcggca ggtggggcgt     300
tggaggaaaa gaaagtctgc caaggcacaa gtaacaggct cacccaactg ggcacttttg     360
aagaccactt tctgagcctg cagaggatgt acaacaactg tgaagtggtc cttgggaact     420
tggaaattac ctatgtgcaa aggaattacg acctttcctt cttaaaaacc atccaggagg     480
tggccggcta tttcctcatt gccctcaaca ccgtggagag aatcccttcg gaggacctgc     540
agatcatcag gggaaatgct ctttatgaaa acacctatgc cttagccatc ctgtccaact     600
atgggacaaa cagaactggg cttagggaac tgcccatgcg gaacttacag gaaatcctga     660
ttggtgctgt gcgattcagc aacaacccca tcctctgcaa tatggatact atccagtgga     720
gggacatcgt ccaaaacgtc tttatgagca acatgtcaat ggacttacag agccatccga     780
gcagttgccc caaatgtgat ccaagctgtc ccaatgaag ctgctgggga ggaggagagg     840
agaactgcca gaaattgacc aaaatcatct gtgcccagca atgttcccat cgctgtcgtg     900
gcaggtcccc cagtgactgc tgccacaacc aatgtgctgc ggggtgtaca gggccccaaa     960
agagtgactg tctggtctgc caaaagttcc aagatgaggc cacatgcaaa gacacctgcc    1020
caccactcat gctgtacaac cccaccacct atcagatgga tgtcaaccct gaagggaagt    1080
acagctttgg tgccacctgt gtgaagaact gcccccgaaa ctacgtggtg acagatcatg    1140
gctcatgtgt ccgagcctgt gggcctgact actacgaagt ggaagaagat ggcatccgca    1200
agtgtaaaaa atgtgatggg ccctgtcgca aagtttgtaa tggcataggc attggtgaat    1260
ttaaagacac actctccata aatgctacaa acatcaaaca cttcaaatac tgcactgcca    1320
tcagcgggga ccttcacatc ctgccagtgg cctttaaggg ggattctttc acgcgcactc    1380
ctcctctaga cccacgggaa ctagaaattc tcaagactgt gaaggaaata acagggtctt    1440
tgctgattca ggcttggcct gaaaactgga ctgacctcca tgcttttgag aacctagaaa    1500
taattcgtgg cagaacaaag caacatggtc agttttctct ggcggttgtc ggcctgaaca    1560
taacatcgct gccgtggcag gttccatcgc tgtcgtggca ggctgtgaca aggcccttgc    1620
accctctggc ccaaaataga gtcagctggg acactgggcc ctgaccttgt aagcttcctg    1680
```

-continued

```
taatgttagc ctgcccatgg caccccaaca gcaagatcct gaagctcaag tttgatccta      1740
acaaaaccac cgctgctgcg gtttctggga gaagcaagca tttattcacc tgcaagatca      1800
catccctaac cttgactttg cttaagagtg ctgaatgaag atcctgtccc taaatcataa      1860
ctcaattctt tgctcaagg aaaatgcact tgtcttcttc caaaaaaaaa aaatcaatat       1920 gcaaatgga atttgaaata aaagcttttc taaaaatg                               1958
```

<210> SEQ ID NO 2
<211> LENGTH: 478
<212> TYPE: PRT
<213> ORGANISM: Rattus norvegicus

<400> SEQUENCE: 2

```
Met Arg Pro Ser Gly Thr Ala Arg Thr Thr Leu Leu Val Leu Leu Thr
  1               5                  10                  15

Ala Leu Cys Ala Ala Gly Gly Ala Leu Glu Glu Lys Lys Val Cys Gln
                 20                  25                  30

Gly Thr Ser Asn Arg Leu Thr Gln Leu Gly Thr Phe Glu Asp His Phe
             35                  40                  45

Leu Ser Leu Gln Arg Met Tyr Asn Asn Cys Glu Val Val Leu Gly Asn
         50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Phe Leu Ile Ala Leu Asn Thr Val
                 85                  90                  95

Glu Arg Ile Pro Ser Glu Asp Leu Gln Ile Ile Arg Gly Asn Ala Leu
            100                 105                 110

Tyr Glu Asn Thr Tyr Ala Leu Ala Ile Leu Ser Asn Tyr Gly Thr Asn
            115                 120                 125

Arg Thr Gly Leu Arg Glu Leu Pro Met Arg Asn Leu Gln Glu Ile Leu
        130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
                165                 170                 175

Ser Met Asp Leu Gln Ser His Pro Ser Ser Cys Pro Lys Cys Asp Pro
            180                 185                 190

Ser Cys Pro Asn Gly Ser Cys Trp Gly Gly Glu Glu Asn Cys Gln
            195                 200                 205

Lys Leu Thr Lys Ile Ile Cys Ala Gln Gln Cys Ser His Arg Cys Arg
        210                 215                 220

Gly Arg Ser Pro Ser Asp Cys Cys His Asn Gln Cys Ala Ala Gly Cys
225                 230                 235                 240

Thr Gly Pro Gln Lys Ser Asp Cys Leu Val Cys Gln Lys Phe Gln Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Asn Cys Pro Arg Asn Tyr Val Val Thr Asp His
    290                 295                 300

Gly Ser Cys Val Arg Ala Cys Gly Pro Asp Tyr Tyr Glu Val Glu Glu
305                 310                 315                 320
```

```
Asp Gly Ile Arg Lys Cys Lys Lys Cys Asp Gly Pro Cys Arg Lys Val
            325                 330                 335
Cys Asn Gly Ile Gly Ile Gly Glu Phe Lys Asp Thr Leu Ser Ile Asn
            340                 345                 350
Ala Thr Asn Ile Lys His Phe Lys Tyr Cys Thr Ala Ile Ser Gly Asp
            355                 360                 365
Leu His Ile Leu Pro Val Ala Phe Lys Gly Asp Ser Phe Thr Arg Thr
            370                 375                 380
Pro Pro Leu Asp Pro Arg Glu Leu Glu Ile Leu Lys Thr Val Lys Glu
385                 390                 395                 400
Ile Thr Gly Ser Leu Leu Ile Gln Ala Trp Pro Glu Asn Trp Thr Asp
            405                 410                 415
Leu His Ala Phe Glu Asn Leu Glu Ile Ile Arg Gly Arg Thr Lys Gln
            420                 425                 430
His Gly Gln Phe Ser Leu Ala Val Val Gly Leu Asn Ile Thr Ser Leu
            435                 440                 445
Pro Trp Gln Val Pro Ser Leu Ser Trp Gln Ala Val Thr Arg Pro Leu
            450                 455                 460
His Pro Leu Ala Gln Asn Arg Val Ser Trp Asp Thr Gly Pro
465                 470                 475

<210> SEQ ID NO 3
<211> LENGTH: 35
<212> TYPE: DNA
<213> ORGANISM: Rattus norvegicus
<220> FEATURE:
<223> OTHER INFORMATION: Reverse primer for RACE

<400> SEQUENCE: 3
gactcgagtc gacatcgatt tttttttttt ttttt                              35

<210> SEQ ID NO 4
<211> LENGTH: 22
<212> TYPE: DNA
<213> ORGANISM: Rattus norvegicus
<220> FEATURE:
<223> OTHER INFORMATION: Forward primer for RACE

<400> SEQUENCE: 4
cgcactcctc ctctagaccc ac                                            22

<210> SEQ ID NO 5
<211> LENGTH: 22
<212> TYPE: DNA
<213> ORGANISM: Rattus norvegicus
<220> FEATURE:
<223> OTHER INFORMATION: Forward primer B  for ERRP

<400> SEQUENCE: 5
cgcactcctc ctctagaccc ac                                            22

<210> SEQ ID NO 6
<211> LENGTH: 20
<212> TYPE: DNA
<213> ORGANISM: Rattus norvegicus
<220> FEATURE:
<223> OTHER INFORMATION: Reverse primer T3 for ERRP

<400> SEQUENCE: 6
attaaccctc actaaaggga                                               20
```

-continued

```
<210> SEQ ID NO 7
<211> LENGTH: 20
<212> TYPE: DNA
<213> ORGANISM: Rattus norvegicus
<220> FEATURE:
<223> OTHER INFORMATION: GAPDH forward pimer

<400> SEQUENCE: 7
accacagtcc atgccatcac                                               20

<210> SEQ ID NO 8
<211> LENGTH: 20
<212> TYPE: DNA
<213> ORGANISM: Rattus norvegicus
<220> FEATURE:
<223> OTHER INFORMATION: GAPDH reverse primer

<400> SEQUENCE: 8
tccaccaccc tgttgctgta                                               20
```

US 6,399,743 B1

ISOLATION AND CHARACTERIZATION OF A RAT EPIDERMAL GROWTH FACTOR RELATED PROTEIN

This application claims priority of provisional application Ser. No. 60/134,200 filed May 14, 1999.

This work has been supported by the Department of Veterans Affairs. The United States Government retains certain rights in this invention.

FIELD OF THE INVENTION

This invention relates to the epidermal growth factor related proteins, polynucleotides encoding these proteins and methods for using these proteins. The cellular machinery involved in mitogenesis is complex, and not yet fully understood. In general, receptors present on the cell surface bind growth factors, resulting in an activated receptor. In particular, tyrosine kinase receptors (TKRs) are endowed with intrinsic tyrosine kinase activity. The activated receptors, in turn, phosphorylate intracellular substrates. These phosphorylated substrates are responsible for a series of events that leads to cell division. This process is generally referred to as "mitogenic signal transduction." The molecular machinery involved in this process is considered to be the "mitogenic signaling pathway."

Growth factors and hormones exert pleiotropic effects on cellular functions, including mitogenic stimulation and modulation of differentiation and metabolism (Ullrich, et al. Cell 61:203–212 (1990); Aaronson, S. A. Science 254: 1146–1153 (1991)). In many cases, these actions are mediated by the interaction of growth factors with cell surface tyrosine kinase receptors (TKRs), which results in enhanced receptor catalytic activity and tyrosine phosphorylation of intracellular substrates (Ullrich, et al., supra, Aaronson, supra). Knowledge of the nature of these second messenger systems is still scanty, although some molecules which associate and/or are tyrosine phosphorylated by TKRs have been identified. These include the γ isozyme of phospholipase C (PLC-7) (Margolis, et al. Call 57: 1101–1107 (1989), Meinsenhelder, et al. Cell 57: 1109–1122 (1989) and Wahl, et al. Mol. Cell. Biol. 9: 2934–2943 (1989)); the p21ras GTPase activating protein (GAP) (Molloy, et al. Nature 342: 711–714 (1989), Kaplan, et al. Cell 61:125–133 (1990), and Kazlauskas, et al. Science 247: 1578–1581 (1990)); the raf serine-threonine kinase (Morrison, et al. Proc. Natl. Acad. Sci. USA 85: 8855–8859 (1988), and Morrison, et al. Cell 58: 649–657 (1989)); the p85 subunit of the phosphatidylinositol 3-kinase (PtdIns-3K); (Coughlin, et al. Science 243: 1191–1194 (1989) Kazlauskas, et al. Cell 58: 1121–1133 (1989), Varticovski, et al. Nature 342: 699–702 (1989), Ruderman, et al. Proc. Natl. Acad. Sci. USA 87: 1411–1415 (1990), Escobedo, et al. Cell 65: 75–82 (1991), Skolnik, et al. Cell 65: 83–90 (1991), Otsu, et al. Cell 65: 91–104 (1991)) and some cytoplasmic tyrosine kinases (Gould, et al. Mol. Cell. Biol. 8: 3345–3356 (1988); Kypta, et al. Cell 62: 481–492 (1990)). These signaling molecules are thought to mediate at least in part the mitogenic effects of TKRs (Ullrich, et al. supra; Aaronson, supra).

However, the Epidermal growth factor (EGF) receptor (EGFR) does not appear to efficiently interact with known second messenger systems (Fazioli, et al. Mol. Cell. Biol. 11: 2040–2048 (1991); Segatto, et al. Mol. Cell. Biol. 11: 3191–3202 (1991)). Thus, there is need to ascertain the mechanism by which the EGFR functions in mitogenesis, and a particular need to identify and characterize the substrate (if any) of the EGFR.

Errors which occur in the mitogenic signaling pathway, such as alterations in one or more elements of that pathway, are implicated in malignant transformation and cancer. It is believed that in at least some malignancies, interference with such abnormal mitogenic signal transduction could cause the cells to revert to normal phenotype.

In addition, reagents useful in identifying molecular components of the mitogenic signaling pathway find utility as tumor markers for therapeutic, diagnostic, and prognostic purposes. Furthermore, identification of how such components differ from normal components in malignant tissue would be of significant value in understanding and treating such malignancies.

EGFR, a 170 kDa transmembrane glycoprotein protein with intrinsic tyrosine kinase activity, which binds EGF family of peptides, plays an important role in controlling cell proliferation and differentiation as was shown by Ullrich et al. supra. The EGFR possesses three functional domains that include extracellular, transmembrane and cytoplasmic. Ligand binding to the extracellular domain of EGFR leads to dimerization and activation of the receptor's intrinsic tyrosine kinase, located in the cytoplasmic domain, triggering a complex array of enzymatic and biological events leading to cell proliferation and differentiation.

Overexpression of EGFR has been associated with many malignancies, including cancers of the stomach and colon. Evidence is accumulating which show that malignant as well as certain normal cells also produce other form(s) of EGFR. For example, A431 human epidermoid carcinoma cells have been shown to produce a truncated EGFR that encodes a 2.8 kb mRNA transcript and is thought to be the result of gene rearrangement in chromosome 7. Likewise, the normal rat liver produces a 2.7 kb mRNA transcript whose 5', but not 3', sequences show 100% homology with the external domain of the full-length rat EGFR. This and other relevant observations suggest that this truncated form of EGFR mRNA, whose protein product is also secreted from the cell, is generated from alternative splicing of the primary EGFR transcript. A shorter 1.8 kb alternative transcript from the human EGFR, which also produces a secreted product, has been isolated from a human placental cDNA library (Reiter J. L., Maihle, N. J. Nucleic Acid Research 24:4050–4056, 1996).

SUMMARY OF THE INVENTION

The present invention is directed toward a polynucleotide sequence, proteins transcribed from the nucleotide sequence, methods for the use of epidermal growth factor receptor related protein (ERRP) as well as probes for the detection of m-RNA, DNA and cDNA of the described nucleotide sequence and monoclonal antibodies directed toward ERRP.

In particular, a cDNA fragment clone of 1583 base pairs with 90–95% sequence homology to mouse epidermal growth factor receptor (EGFR) and a truncated rat EGFR was isolated. The full length cDNA revealed 1958 base pairs (SEQ ID No: 1) that contained 227 base pairs of 5' untranslated region and an open reading frame encoding 478 amino acids (SEQ. ID NO: 2) followed by 290 base pairs of an untranslated region. The full length cDNA showed an 84% and 91% homology, respectively, to a rat truncated EGFR and the mouse EGFR. The product of the newly isolated DNA is referred to as ERRP (EFG-Receptor Related Protein). In a Northern-blot analysis with poly A+RNA from different rate tissues, ERRP cDNA hybridized strongly to a mRNA transcript of about 1.8 Kb. Maximal expression was noted in the small intestine, followed by colon, liver gastric mucosa and other tissue. Transfection of ERRP cDNA in HCT-116 cells, a colon cancer cell line, markedly inhibited (40–60%) proliferation in monolayer and soft agar and also attenuated EGFR tyrosine kinase activity compared to vector-transfected control cells. Proliferation of the vector-transfected control, but not ERRP transfected HCT cells could be stimulated by TGF-α ($10^{-10}\mu$ and $10^{-9}\mu$). The over expression of ERRP in HCT-116 cell delayed tumor growth in SCID mice xenografts. The ERRP cDNA represents a new member of the EGFR gene family and the protein product plays a key role in modulating the function of EGFR.

BRIEF DESCRIPTION OF THE DRAWINGS

FIGS. 1(a), 1(b): Description of the aligned nucleotide and amino acid sequence of ERRP. (SEQ. ID No: 1 and SEQ. ID NO: 2)

FIG. 2: Description of the nucleotide sequence of ERRP. (SEQ. ID NO: 1)

FIG. 3: Description of the amino acid sequence of ERRP. (SEQ. ID NO: 2)

FIG. 4: Schematic representation of ERRP cDNA showing its homology to a rat truncated EGF-R (T-EGER).

FIG. 9: Clonogenic assay in soft agar showing changes in proliferation of HCT-116 following transfection with either ERRP cDNA (clones 1 and 2) or the vector only (controls). One milliliter containing 100 cells were sandwiched between 1.8% and 0.3% agarose in DMEM/10% FBS. Plates were incubated at 37° C. for 14 days. Values represent mean ±SEM of 6 observations.

FIG. 11: Illustration of the effect of ERRP-fusion protein on EGF-R Tyr-K activity in HCT-116 cells. Cells were exposed to either 5 μg of ERRP fusion protein bound to MBR or MBP alone for 5 minutes at 37° C.

FIG. 12: Comparison of the effects of ERRP-fusion protein of proliferation of HCT-116 cells. Cells were exposed to a concentration of 3, 70 and 300 ng/ml of ERRP fusion protein for 48 hours.

FIG. 13: Tumor growth in SCID mouse xenografts showing the difference in the rate of growth of tumors formed by HCT-116 cells, transfected with ERRP cDNA (clones 1 and 2) or the vector only (control).

FIG. 14: Autoradiograph showing changes in the activation of EGF-R tyroisne kinase in HCT-116 cells following transfaction with ERRP cDNA (clones 1 and 2, marked as A1 and A2) or the vector only (control) as determined by the extent of phosphophylation of acid-denatured enolase. The cell maintained in DMEM cell medium containing 0.1% FBS.

DETAILED DESCRIPTION OF THE INVENTION

Figure 6:
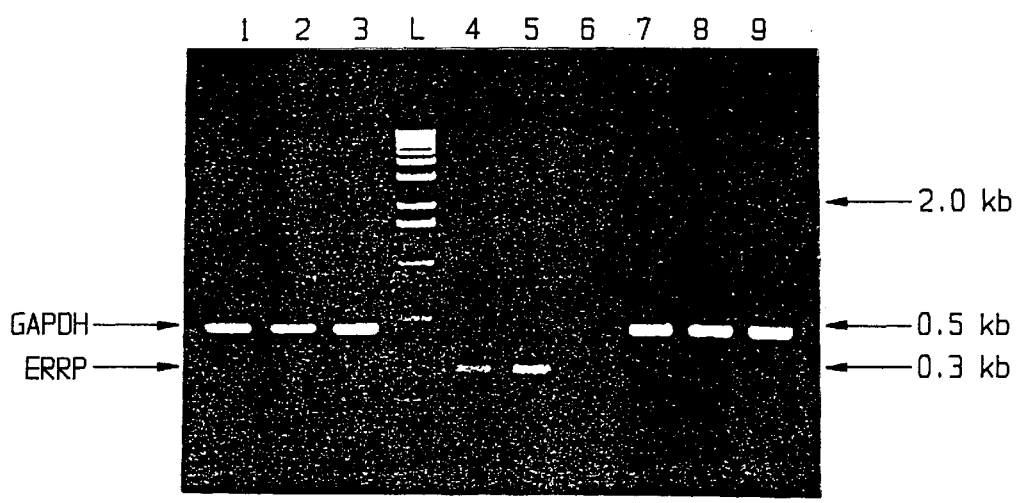
FIG. 6: RT-PCR reaction showing changes in mRNA levels of ERRP and GAPDH in the control (vector-transfected) and ERRP cDNA transfected (clones 1 and 2) HCT-116 cells. RT-PCR was performed with primers for ERRP and GAPDH simultaneously (lanes 1–3) or with primers for ERRP (lanes 4–6) or GAPDH (lanes 7–9). Lanes 1, 2 and 3 represent clones 2, 1 and controls respectively. Lanes 4, 5 and 6 represent clones 2, 1 and control. Lanes 7, 8 and 9 represent clones 2, 1 and controls. Lane L represents DNA ladder.

It has been demonstrated that stimulation of gastric mucosal proliferative activity, whether the result of aging, injury or the administration of gastrin, bombesin or EGF to young adult rats, is associated with a rise in tyrosine phosphorylation of a membrane protein with a molecular mass of 55 kDa. A similar phenomenon has also been observed in the colonic mucosa of rats after administration of either gastrin or the colonic carcinogen azoxymethane. These and other relevant observations led us to suggest that the 55 kDa phosphotyrosine mucosal membrane protein, which we have referred to as pp55, may play a role in modulating gastrointestinal mucosal cell proliferation.

In order to characterize pp55 and to study its functional properties, polyclonal antibodies raised against this protein were used to screen a cDNA expression of a library generated from rat gastro-duodenal mucosal mRNA. A computer search of the nucleotide sequences of one of the candidate cDNA clones showed a significant homology with the extracellular domain of the mouse EGFR (epidermal growth factor receptor) and a rat truncated EGFR. The latter also possesses considerable homology with the extracellular domain of EGFER (10). We refer to the product of this newly isolated cDNA as ERRP (EGRR Related Peptide).

During the course of screening the cDNA expression library with pp55 antibodies, we isolated a cDNA fragment clone of 1583 base pairs (bp) which showed a 95% sequence homology to the extracellular domain of the mouse EGFR and an 92% homology to a truncated rat EGFR. We refer to the product of this clone as ERRP (EGRR Related Protein). The 1583 bp cDNA fragment possessed the "initiation" ATG codon, but lacked the termination codon. In view of this, RACE was applied to obtain the 3'-terminal end, which resulted in a 375 bp fragment with TGA "termination" codon and the 3' poly A tail. The full-length cDNA thus obtained consisted of 1958 bp (SEQ. ID NO: 1) which contained 227 bp 5' untranslated region and an open reading frame (ORF) that coded for 478 amino acids (SEQ. ID NO: 2) which showed a 84% and 91% homology, respectively, with the rat truncated EGFR and the external domain mouse EGFR. It also possessed a little over 80% homology with the external domain of the human EGFR. However, the first 24 amino acids of the ORF were similar but not identical to those found in the signal peptide of human EGFR. Additionally, a region of the 3' end (referred to as U; nucleotides 1580–1661) encoding 27 amino acids showed no homology with any known sequence in the current data base. The results suggest that ERRP is a new member of the EGFR family.

The full-length cDNA was isolated and consists of 1958 base pairs (bp) (SEQ. ID NO: 1) that included 227 bp 5' untranslated region (UTR) and a putative open reading frame (ORF) of 1437 nucleotides encoding 478 amino acids, and a 290 nucleotide 3' UTR as is shown in FIG. 4.

Figure 5:
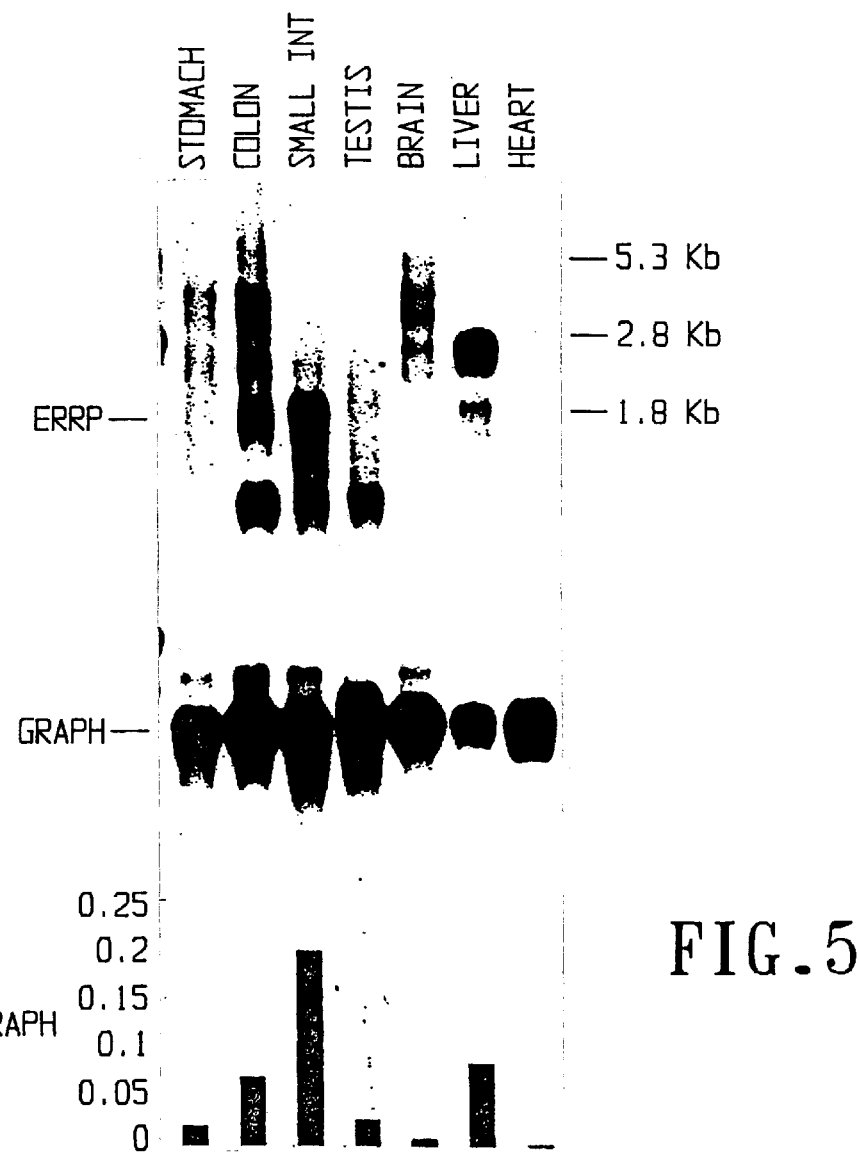
FIG. 5: Northern-blot analysis showing the mRNA transcript size of ERRP in different tissues in rats. Each lane contains 1 μg poly A+ RNA. The membrane was also probed with GAPDH. Changes in relative concentration of ERRP mRNA, expressed as ratio of ERRP to GAPDH, are shown at the bottom of the figure.
Figure 10:
FIG. 10: Illustration of the changes in EGF-R tyrosine kinase (Tyr-K) actively in HCT-116 following transfection with ERRP cDNA (clones 1 and 2). Control cells were transfected with the vector.

To determine the expression of ERRP, Northern-blot analysis was performed with poly A+ RNA from different tissues of the gastrointestinal tract as well as from the liver, brain, heart and testes. Expression of ERRP mRNA varied considerably between the tissues as is shown in FIG. 5. ERRP cDNA hybridized strongly to a mRNA transcript of about 1.8 kb with maximal expression noted in the small intestine, followed by colon, liver, gastric mucosa and other tissues. No hybridization of ERRP cDNA to 1.8 kb mRNA transcript was observed in testes, brain and heart. In addition to the 1.8 kb mRNA transcript, ERRP cDNA also reacted strongly with 2.8 kb transcript in the liver, and with 0.6, 2.8 and 5.0 kb mRNAs in certain tissues, most notably in the colon. The transcript size 5.0 kb may represent EGFR. However, no expression of ERRP mRNA was observed in the heart as is shown in FIG. 5.

To determine putative functional properties of ERRP, cDNA for ERRP was stably transfected in HCT-116 cells, a colon cancer cell line. Four ERRP-positive clones, as evidenced by Northern-blot analysis with poly A+RNA, were selected. For further verification of ERRP transfection, RNA extracted from cells grown from these clones were subsequently subjected to RT-PCR analysis with primers generated from 1.6 kb fragment of the full-length 1.95 kb ERRP. RT-PCR analysis revealed ERRP mRNA in clones #1 and #2 with minimal to no-detectable levels in the other two clones as is shown in FIG. 6. ERRP expression was higher in clone #1 than clone #2. No ERRP mRNA was detected in control cells (transfected with the vector alone). In contrast, no apparent difference in GAPDH mRNA levels were found among the different clones.

Figure 7:
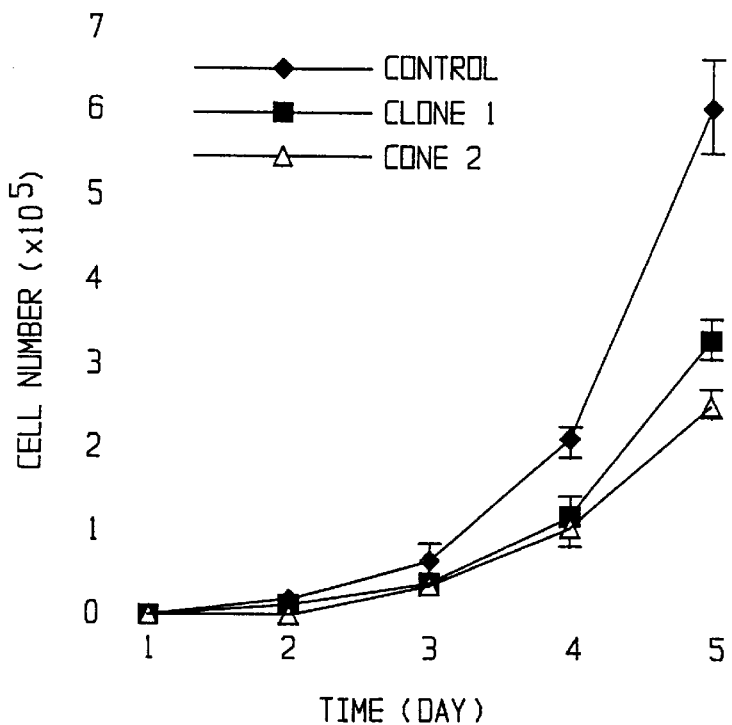
FIG. 7: Effect of ERRP cDNA transfection on proliferation of HCT-116 cells. The control (vector-transfected) and ERRP cDNA transfected cells were maintained in DMEM/10% FBS. Each value represents mean ±SEM for 6 observations.

To determine putative functional properties of ERRP, the rate of proliferation of ERRP-expressed cells (Clones #1 and 2) was compared with control cells. Results from a 5-day cell culture study revealed that although cells from all three clones grew essentially at the same rate during the first 3 days, the rate of proliferation in ERRP transfected cells decreased markedly during the next two days in culture when compared with controls as is shown in FIG. 7. To demonstrate that the inhibition of HCT-116 cell proliferation by ERRP expression was not due to a "positive effect" of the inserted DHA, we assayed three other distinct ERRP-transfected HCT-116 cell subclones. Each of these subclones exhibited decreased proliferation relative to controls.

Figure 8:
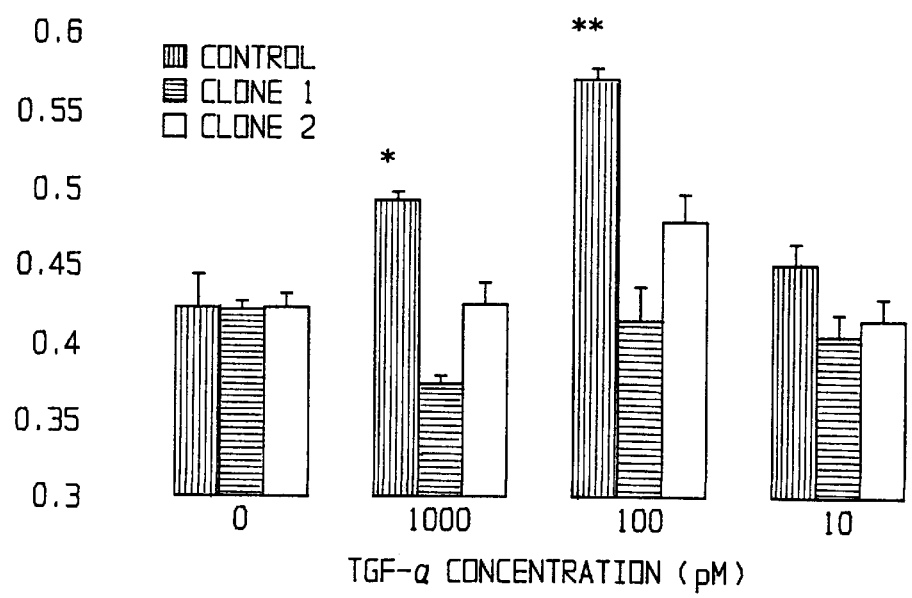
FIG. 8: Effects of increasing concentrations of TGF-α on proliferation of ERRP cDNA or vector-transfected HCT-116 cells. Values represent mean ±SEM for 6.

TGF-α-induced proliferation of ERRP transfected and control HCT-116 cells was examined. In this investigation, 48 h serum-starved (0.1% FBS) cells from clones 1 and 2 as well as those from the vector-transfected clone were maintained for 24 h in the absence (basal) or presence of increasing concentration of TGF-α ($10^{-11}$ to $10^{-9}$M). Results revealed that whereas TGF-α at a dose of either $10^{-9}$ or $10^{-10}$M significantly stimulated proliferation in control cells, it had no effect on cells from either clone 1 or clone 2 as is shown in FIG. 8.

To determine whether transfection of ERRP in HCT-116 cells will affect the tumorigenic property of this cell line, extent of proliferation of clones 1 and 2 and their control counterpart (vector transfected cells) was examined in soft agar over a period of 14 days. As shown in FIG. 9, transfection of ERRP in HCT-116 cells markedly decreased their ability to grow in soft agar. Number of colonies formed by clones 1 and 2 were 65% and 40% lower, respectively, compared to the control clone. Size of the colonies formed by clone 1 or 2 was also found to be considerably smaller than those formed by the vector-transfected control clone.

To examine the antiproliferative effect of ERRP by the inhibition of the intrinsic tyrosine kinase activity of EGF-R. As is shown in FIG. 14 basal EGF-R tyrosine kinase activity in ERRP-overexpressed HCT-116 cells (clones 1 and 2) was about 50–60% below the control cells.

Figure 15:
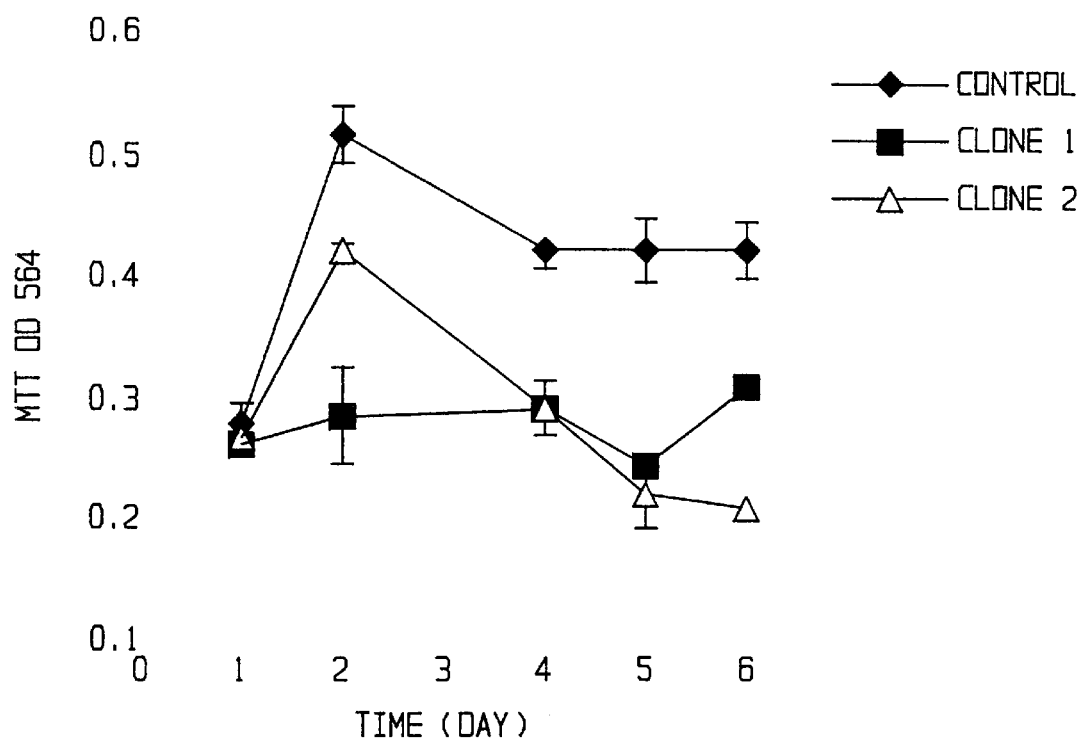
FIG. 15: Effect of serum starvation (0.1% FBS) on proliferation of ERRP-overexpressed (clones 1 and 2) and vector transfected (control) HCT-116 cells.

Serum starvation also resulted in a marked 50–70% inhibition in proliferation of ERRP-transfected HCT-116 cells (clones 1 and 2) compared to the vector-transfected control cells as seen in FIG. 15.

The role of ERRP in regulating EGF-R Tyr-K activity was determined by raising an ERRP fusion protein in E. coli. Purified ERRP-fusion protein was bound to its carrier MBP (molecular binding protein, then utilized to study its effects on EGF-R Tyr-K activity in HCT-116 cells, as seen in FIG. 11. When HCT-116 cells were exposed to 5 μg of MBP-bound ERRP for 5 minutes at 37° C. a marked reduction (80–90%) in EGF-R Tyr-K activity was observed when compared to HCT-116 cells exposed to either MBP alone or to control cells.

The antiproliferation effect of ERRP-fusion protein was determined by exposing HCT-116 cells to ERRP-fusion protein for 48 hours. As is seen in FIG. 12, exposure of HCT-116 cells to the ERRP fusion protein for 48 hours reduced proliferation by 25–30% compared to control cells.

To determine the tumorigenic properties of ERRP, the growth rate of tumors induced by HCT-116 cells, was examined in SCID mouse xenografts. Groups of SCID mice were injected with either $5\times10^6$ HCT-116 cells (clone 1 or 2) per flank or $5\times10^6$ HCT-116 cells (control, transfected with vector) per flank. Tumor growth was monitored and when the tumor(s) attained the size of approximately 1800 mg, the mice were killed. It was observed that in mice injected with control cells, the tumor(s) attained the required weight on the $24^{th}$ day after injection, whereas with clone 1 or 2, it took 14–16 days longer for tumor(s) to grow to that size as is seen in FIG. 13. Tumor growth was slowest for clone 1 transfected cells as was colony formation in soft agar.

The ERRP was isolated and characterized and the fusion protein made in the following example.

Methods

Isolation of RNA: Total RNA was isolated from different tissues and colon carcinoma cell line HCT-116 utilizing RNA-STAT solution (Tel-Test, Friendswood, Tex.) according to the manufacturer's instruction. P, poly A+ was isolated from total RNA by oligo(dT) cellulose chromatography according to the instructions provided by GIBCO-BRL (Gaithersburg, Md.).

Construction of cDNA expression library and screening: Poly A+ RNA, isolated from mucosal scrapings from the gastro-duodenal region of the gastrointestinal tract was utilized for this purpose. An unamplified cDNA expression library was constructed using the EcoRI cloning sites of the λg11 vector system in Y1090r-strain according to the conditions recommended by Stratagene (La Jolla, Calif.). The ligated vector-insert was packaged using Giga-Pack bacterial extracts supplied by Stratagene. The library thus constructed contained $3\times10^6$ pfu (plaque forming units) per ml. Non-recombinant phage associated with the library was about 4%. The reason for constructing an unamplified mucosal library was to minimize the analysis of identical positive clones.

Six duplicate IPTG-treated nitrocellulose filters containing the imprint of 50,000 plaques were washed with PBS-0.1% Tween-20, and left in a blocking buffer (PBS containing 7% nonfat dry milk, 0.5% BSA and 0.1% Tween-20). Membranes were then washed at room temperature in PBS-0.1% Tween-20, and subsequently incubated for 2 h at room temperature with pp55 antibodies (1:5000 final dilution) which were pre-adsorbed six times with *E. coli* lysate protein according to the protocol provided by Strategene. Bound antibody was visualized by the enhanced chemiluminescence (ECL) detection system (Amersham) according to the manufacturer's instruction.

Sequence analysis: DNA from one of the positive plaques (referred to here as ERRP) was isolated and purified. Restriction analysis by EcoRI showed its size to be about 1.6 kb. This was subcloned into EcoRI sites of pBluescript (KS+) vector and subsequently sequenced by the dideoxy chain termination method at the Core Facility of the Center for Molecular Medicine and Genetics, Wayne State University, Detroit. The nucleotide sequence, thus obtained, was compared with known sequences in GenBank using the NCBI BLAST search program.

Rapid Amplification of cDNA Ends (RACE): Since the candidate cDNA under study lacked the termination codon, RACE was utilized to obtain the 3' end in the following manner. Briefly, 1 μg Poly A+ from rat small intestinal mucosa was heat denatured at 65° C. for 3 min and reverse transcribed into a single strand cDNA according to the instruction provided by GIBCO-BRL (Gaithersburg, Md.) in a 20 μg reaction mixture [50 mM Tris-HCl, pH 8.15, 1 mM each dNTP, 10 mM dithiothreitol, 6 mM $MgCl_2$ 40 mM KCl, 10 U Rnasin (Promega, Madison, Wis.) 10 U AMV reverse transcriptase (GIBCO-BRL)] 0.5 μg of oligo-dT primer [5' GACTCGAGTCGACATCGATTTTTTTTTTTTTTTT-3'] (SEQ. ID NO: 3) containing XhoI, SalI, and ClaI restriction sites. The mixture was incubated at 41° C. for 2 h and the product was subsequently used for amplification of 3'-end of 1.6 kb fragment of ERRP. The reaction mixture in 50 μl contained: 1 μl of first strand cDNA, 3'-end primer [5'-CFCACTCCTCCTCTAGACCCAC-3'] (SEQ. ID NO: 4) and (dT) 17-adaptor [25 pmol each], 10% dimethylsulfoxide, 1.5 mM of each dNTP. The mixture was heat denatured for 5 min at 95° C., annealed for 2 min at 53° C. in the presence of 2.5 U of Taq DNA polymerase followed by extension for 40 min at 75° C. The PCR reaction for amplification was carried out for 40 cycles using a step program (denaturation at 94° C. for 40 sec; annealing at 53° C. for 2 min and extension at 72° C. for 3 min) followed by a 15 min final extension at 72° C.

The PCR products from above were directly ligated into pCRII vector (TA cloning kit, Invitogen Corp.), followed by transformation of electro-competent *E. Coli* DH5α cells with one tenth (1/10) of the ligation DNA. Approximately 10,000 independent bacterial colonies were screened by colony hybridization methodology using PCR amplified 3' end of ERRP cDNA (SEQ. ID NO: 1) (from positions 1444 to 1578) as probe. Several independent colonies were identified, followed by the secondary screening in order to obtain purified plasmids.

Northern-blot analysis Aliquots of one microgram of poly $A^+RNA$ isolated from different tissues were electrophoresed in a 1.5% agarose gel containing 2.2 M formaldehyde. After electrophoresis, RNA was transferred to a nylon or nitrocellulose membrane by capillary blotting and subsequently exposed to an UV cross-linker (Strategene, La Jolla, Calif.) for 30 sec (autocross) and prehybridized in 5×SSC (1×SSC, 0.15 M sodium chloride, 0.015 M sodium citrate) containing 2% blocking reagent (Boehringer-Mannheim), 50% formamide and 0.1% sodium lauroylsarcosine and 0.02% sodium dodecyl sulfate (SDS) for 2 h at 50° C.

Hybridization with $^{32}P$-labeled RNA probe of 1.5 kb cDNA under study was performed for 18 h at 50° C. in the same solution. The plasmid pBK containing 1.6 kb cDNA was linearized by digesting with PstI. The antisense RNA probe was then synthesized using 1 μg of linearized plasmid with T3 RNA polymerase with the use of a commercial kit (StripAble RNA, Ambion, Austin, Tex.). Glyceraldehyde-3-phosphate dehydrogenase (GAPDH) was used as an internal control. GAPDH RNA probe was prepared by transcribing 1 μg of pTR1-GAPDH (rat; Ambion) with T3 RNA polymerase. The probes were labeled with $[(\alpha-^{32}P]UTP$ according to the manufacturer's instructions.

Stable transfection of ERRP and Cell Culture: The cDNA 1.6 kb under study, which was subcloned in pBluescript (KS+) vector, was digested with Pvu II followed by EcoRI. The resultant fragment was inserted into EcoRI/EcoRV cloning sites of the eukaryotic expression vector pcDNA 3.1 (+) containing neomycin-resistant gene [Invitrogen]. The resultant construct and the vector DNA (without cDNA insert) were used to stably transfect a human colon cancer cell line HCT-116.

HCT-116 cells, maintained in Dulbecco's modified Eagle's medium (DMEM) supplemented with 10% fetal bovine serum (FBS), 100 U/ml streptomycin-penicillin and 0.25 μg/ml amphotericin B, were transfected with either 1.6 kb portion of the 1.8 kb full-length ERRP cDNA or the vector alone (control) by lipofectin according to the manufacturer's instruction (GIBCO-BRL) in the presence of neomycin (geneticin G418; GIBCO-BRL). Neomycin-resistant colonies were selected in the presence of 0.6 mg/ml G418. Colonies were picked at random and grown as individual cell lines in the presence of 0.4 mg/ml G418. Each cell line was subjected to RT-PCR analysis according to our standard protocol. Briefly, 3 μg of total RNA was reverse transcribed into first strand cDNA in a 20 μl reaction mixture containing: 2 μl 10×PCR buffer, 5 mM $MgCl_2$, 1 mM of each dNTP, 20 U RNAse inhibitor, 2.5 μM of Oligo (dT)16 and 2.5 MuLV reverse transcriptase. The reaction mixture was incubated at room temperature for 10 min followed by incubations at 42° C. for 30 min, 95° C. for 5 min. and finally 50° C. for 5 min. First strand cDNA thus obtained was used for PCR analysis utilizing Amplitaq DNA polymerase (Perkin Elmer) and 0.15 μM of upstream primer [5'-CGCACTCCTCCTCTAGACCCAC-3'] (SEQ. ID NO: 5) (taken from ERRP sequence) and 0.15 μM downstream primer [5'ATTAACCCTCACTAAAGGGA3'] (SEQ. ID NO: 6) taken from pcDNA 3.1(+) vector, and/or GAPHDH upstream [5'-ACCACAGTCCATGCCATCAC-3'] (SEQ. ID NO. 7) and downstream primers [5-TCCACCACCCTGTTGCTGTA-3'] (SEQ. ID NO. 8). The PCR reaction for amplification was carried out for 35 cycles using a step program (denaturation at 95° C. for 1 min; annealing at 63° C. for 1 min. and extension at 72° C. for min. followed by a 15 min. final extension at 72° C. The reaction product was electrophoresed on an 1.5% agarose gel, subsequently stained with ethidium bromide.

Tyrosine kinase activity of EGFR: The enzyme activity was determined in lysed cells according to our standard protocol. Briefly, plated cells were lysed in lysis buffer [50 mM tris-HC], pH 7.4, 100 mM NaCl, 2.5 mM EDTA, 1% Triton X-100, 1% Nonidet P40, 2.5 nM $Na_3VO_4$, 25 μg/ml aprotinen, 25 μg/ml leupeptin and 50 μg/ml soybean trypsin inhibitor] using a Dounce homogenizer. The homogenate was stirred in a mechanical rotator for 30 min at 4° C. and subsequently centrifuged at 10,000×g for 10 min at 4° C.

Supernatant was assayed for protein content using the Bio-Rad protein assay kit (Bio-Rad, hercules, Calif.). Aliquots of cell lysate containing 1 mg protein were incubated overnight at 4° C. with 1 μg polyclonal antibody to EGFR (Santa Cruz Biotechnology, Santa Cruz, Calif.). The immune complexes were precipitated with Sepharose bound protein-G, washed several times with kinase buffer (25 mM HEPES, pH 7.5, 5 mM mnCl$_2$, 2.5 mM MgCl$_2$, 0.5 mM, ditheothreitol, 0.5 mM Na$_3$VO$_4$, 10 mM p-nitrophenol phosphate, 5 mM β-glyverol phosphate). The immunoprecipitates were resuspending in 30 μl kinase reaction buffer [HEPES, pH 7.5, 10 mM MnCl$_2$, 2.5 mM MgCl$_2$, 0.1 M Nacl 150 mM Ncl, 0.5 mM ditheothreitol, 0.5 mM Na$_3$VO$_4$, 10 mM p-nitrophenol phosphate, 5 mM β-glyverol phosphate and 0.1 mM ATP] and assayed for tyrosine kinase activity by measuring $^{32}$incorporation from [γ-$^{32}$P]ATP into acid-denatured enolase.

I claim:

1. A purified epidermal growth factor receptor related protein (ERRP) having the amino acid sequence of SEQ. ID NO: 2.

2. The purified protein of claim 1, wherein said protein consists of residues 1–478 of SEQ. ID NO: 2.

3. The purified protein of claim 1, characterized as having anti-proliferation activity properties.

4. The purified protein of claim 1, characterized as possessing the property of inhibiting epidermal growth factor receptor (EGFR) activation and proliferation of cells expressing EGFR.

* * * * *